(12) United States Patent
Ng et al.

(10) Patent No.: US 7,700,333 B2
(45) Date of Patent: Apr. 20, 2010

(54) IMMOBILIZATION OF CELLS IN A MATRIX FORMED BY BIOCOMPATIBLE CHARGED POLYMERS UNDER LAMINAR FLOW CONDITIONS

(75) Inventors: San San Susanne Ng, Singapore (SG); Hanry Yu, Singapore (SG)

(73) Assignee: Agency for Science Technology & Research, Centros (SG)

( * ) Notice: Subject to any disclaimer, the term of this patent is extended or adjusted under 35 U.S.C. 154(b) by 485 days.

(21) Appl. No.: 10/899,727

(22) Filed: Jul. 26, 2004

(65) Prior Publication Data

US 2006/0019361 A1   Jan. 26, 2006

(51) Int. Cl.
*C12N 11/04* (2006.01)
*C12N 11/08* (2006.01)

(52) U.S. Cl. .................. 435/177; 435/182; 435/180; 427/213.34; 514/963

(58) Field of Classification Search ........................ None
See application file for complete search history.

(56) References Cited

U.S. PATENT DOCUMENTS

| 6,916,640 B2 * | 7/2005 | Yu et al. ............ 435/182 |
| 2002/0094569 A1 * | 7/2002 | Yu et al. ............ 435/325 |
| 2003/0044766 A1 | 3/2003 | Scholz et al. |

FOREIGN PATENT DOCUMENTS

WO   WO 2004/101743   11/2004

OTHER PUBLICATIONS

Alaris Medical Systems IVAC P6000 Directions for Use. 6001FAOPT73 Issue 6. Downloaded from Internet Apr. 2007.*
Tan et al., (Tissue Engineering. 2003;9(2):255-267) (cited in Applicant's IDS of Oct. 28, 2004).*
Tan et al., "Layer-by-layer microfluidics for biomimetic three-dimensional structures", Biomaterials, 2004, vol. 25, 1335-64.
Tan et al., "Microfluidic patterning of cells in extracellular matrix biopolymers: effects of channel size, cell type, and matrix composition on pattern integrity", Tissue Engineering, 2003, vol. 9(2), 255-67.
Liu et al., "Hybrid bio/artificial microdevices", Biomedical Microdevices, 2002, vol. 4(4), 257-66.
Harimoto et al., "Novel approach for achieving double-layered cell sheets co-culture: overlaying endothelial cell sheets onto monolayer hepatocytes utilizing temperature-responsive culture dishes", J. Biomed. Mater. Res., 2002, vol. 62(3), 464-70.
Cooper et al., "C2C12 co-culture on a fibroblast substratum enables sustained survival of contractile, highly differentiated myotubes with peripheral nuclei and adult fast myosin expression", Cell Motil. Cytoskeleton, 2004, vol. 58(3), 200-11.

(Continued)

*Primary Examiner*—Cherie M Woodward
(74) *Attorney, Agent, or Firm*—Stout, Uxa, Buyan & Mullins, LLP; Carlos A. Fisher

(57) ABSTRACT

This invention relates to a method for immobilizing cells under laminar flow conditions in a matrix formed by biocompatible charged polymers, to a flow device for the use with the method of the present invention, and to uses of the polymer matrices containing the cells immobilized using the method of the present invention.

33 Claims, 9 Drawing Sheets

OTHER PUBLICATIONS

Fair et al., "Induction of hepatic differentiation in embryonic stem cells by co-culture with embryonic cardiac mesoderm", Surgery, 2003, vol. 134(2), 189-196.

Schumm et al., "Enhanced viability and neuronal differentiation of neural progenitors by chromaffin cell co-culture", Dev. Brain Res. 2002, vol. 137(2), 115-25.

Takayama et al., "Patterning cells and their environments using multiple laminar fluid flows in capillary networks", Proc. Natl. Aca. Sci, 1999, vol. 96, 5545-48.

McDonald et al., "Fabrication of microfluidic systems in poly(dimethylsiloxane)", Electrophoresis, 2000, vol. 21(1), 27-40.

Wen et al., "Microcapsules through polymer complexation I. Complex coacervation of polymers containing a high charge density", Biomaterials, 1991, vol. 12, 374-84.

Wen et al., "Microcapsules through polymer complexation Part 3: encapsulation and culture of human Burkitt lymphoma cells in vitro", Biomaterials, 1995, vol. 16, 325-35.

Chia et al., "Hepatocyte encapsulation for enhanced cellular functions", Tissue Engineering, 2000, vol. 6(5), 481-95.

Wallace et al., "Collagen gel systems for sustained delivery and tissue engineering", Advanced Drug Delivery Reviews, 2003, vol. 55, 1631-49.

Toh, YC et al. "A configurable Three-Dimensional Microenvironment in a Microfluidic Channel for Primary Hepatocyte Culture" Assay and Drug Development Tehcnologies, Apr. 2005, vol. 3, No. 2: 169-176 (abstract only).

Wei tan, M.S. et al. "Microfluidic Patterning of Cells in Extracellular Matrix Biopolymers: Effects of Channel Size, Cell Type, and Matrix Composition on Pattern Intergrity" Tissue Engineering, 2003, vol. 9 (2):255-267.

\* cited by examiner

2C

2D

Fig. 3
Fig. 3A
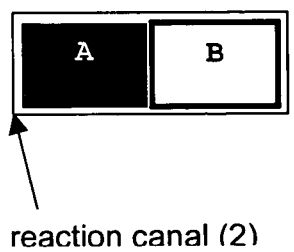
reaction canal (2)
Fig. 3B
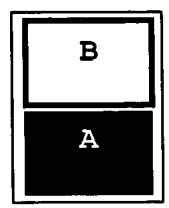
Fig. 3C
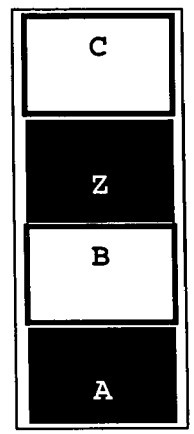
Fig. 3D
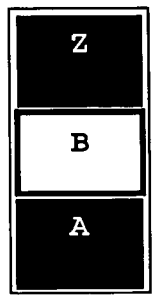
Fig. 3E
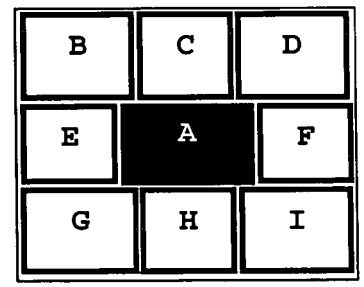

100 μm    100 μm

IMMOBILIZATION OF CELLS IN A MATRIX FORMED BY BIOCOMPATIBLE CHARGED POLYMERS UNDER LAMINAR FLOW CONDITIONS

The invention relates to a method for immobilizing cells under laminar flow conditions in a polymer matrix formed by biocompatible charged polymers, to a flow device for the use with the method of the present invention, and to uses of the polymer matrices containing the cells immobilized using the method of the present invention.

BACKGROUND OF THE INVENTION

Tissues in vivo have highly organized complex three-dimensional structures that comprise of heterogeneous cell populations and extra-cellular matrix (ECM). In mammals, the ECM can surround cells as fibrils, tubes and channels that contact the cells on all sides, or as a sheet called the basement membrane that cells 'sit on'. The ECM is normally composed of proteins and polysaccharides to provide mechanical support and a biochemical barrier. A modified form of ECM, for example, appears in the form of bone. Research has shown that the functioning of cells is very much influenced by cell extracellular matrix. Some cells can only grow and prolong their cell survival in co-cultures of different cell types. However, co-cultures have been limited by the inability to manipulate or control the interaction of the different cells in the culture due to the lack of a suitable matrix for these cells.

Thus, because of the importance of a matrix for cell growth, it is a major goal of tissue engineering to recreate ECM structures that better mimic this matrix surrounding the cells in vivo, in particular to mimic the matrix of in vivo tissue.

The application of microtechnology in tissue engineering, which include micromachining, photolithography and sort lithography, has allowed the patterning of cells in size scales of micrometers relevant to the matrix of tissues. However, most work demonstrated previously was in creating two-dimensional patterns of single cells or multiple cell types, and few of three-dimensional patterning in which different layers are stacked one above the other to create an in vivo like three-dimensional structure for cells.

Wei Tan, M. S. and T. A. Desai (Biomaterials, 2004, Vol. 25, P. 1355-1364) describe reconstituted biopolymer matrices for the creation of three-dimensional patterns inside channels. Layer by layer micromolding in capillaries (MIMIC) via cell-matrix contraction has allowed the deposition of heterotypic cell layers in z-dimensions. Thereby, the biopolymer matrix is immobilized on the surface by binding the biopolymer matrix via a chemical linker to the surface of the carrier. However, this approach is limited to the patterning of one cell layer at a time and lacks precise control of the matrix surrounding the live cells.

In another approach of the same authors (Wei Tan, M. S. and T. A. Desai, Tissue Engineering, 2003, Vol. 9, No. 2, P. 255-267) native collagen and mixtures of collagen with chitosan or collagen, chitosan and fibronectin were used to create matrices for embedding human lung fibroblasts and human umbilical vein endothelial cells therein. Gelation took place in channels coated with BSA in which the polymer-cell mixture was pumped. However, long gelation times and missing means to control the gelation limit the use of this method in creating ECM like structures.

Another approach is the three-dimensional photolithography of hydrogels containing living cells (Liu and Bhatia, Biomedical Devices 2002, Vol. 4(4), P. 257-266). However, the cell toxicity of the photoinitiatior employed in photopolymerization is a major problem of this method.

Since the functionality of some kind of cells and the ability to grow depends to a great extent on the matrix surrounding the cell, there is still a need of effective systems for creating such matrices for different cell species.

SUMMARY OF THE INVENTION

In one aspect, the present invention refers to a method for immobilizing at least one cell species in a matrix formed by biocompatible charged polymers. This method comprises:

providing a first charged polymer and a second charged polymer, wherein the at least one cell species is embedded in the second charged polymer and wherein the first charged polymer has an electrical charge opposite to that of the second polymer, and reacting the polymers under laminar flow conditions to form a matrix for the at least one or at least two cell species.

The method of the present invention of reacting oppositely charged polymers under laminar flow conditions is an efficient means of forming polymer matrices containing living cells rapidly in situ without long polymerisation times. Furthermore, the reaction of the present invention takes place under cell friendly and aqueous conditions that are non-toxic to cells. In addition, the polymer matrix formed using the method of the present invention can be easily modified by the use of different polymer combinations as well as reaction conditions for the oppositely charged polymers and the laminar flow conditions. A greater mechanical stability is achieved due to the specific polymerisation reaction by virtue of complex coacervation. Cell culturing in a three-dimensional matrix formed by laminar streams of polymers flowing side by side in the same plane as well as stacked one above the other allows a more complex patterning and thus mimic of conditions that can be found for cells in living tissue.

BRIEF DESCRIPTION OF THE DRAWINGS

FIG. 2A shows a top view of a flow device in which the flow device has three inlet openings 3A, 3B, 3C and one outlet opening 4. FIG. 2B shows a side view of the flow device in FIG. 2A. Unlike the canals 5 in FIG. 1B, in FIG. 2B the canals 5 connecting the openings (3, 4) with the reaction canal 2 are arranged transversely to the reaction canal 2. Other examples of flow devices are shown in FIGS. 2C and 2D. FIG. 2C shows a flow device with two inlet (3A and B) and two outlet openings (4A and B) whereas FIG. 2D shows a flow device with three inlet (3A, B and C) and three outlet openings (4A, B and C).

FIG. 3 shows rectangular reaction canals 2 (thin black line around the rectangle) of flow devices in which alternated laminar polymer streams (squares within the canal) are schematically shown. In these FIGS. 3A to E, layers B to I (white square with black border) represent laminar polymer streams of a second charged polymer which can contain at least one or two cell species. Layers A and Z (black square) represent laminar polymer streams of a first charged polymer (wherein A and Z can be the same polymer but can also be different polymers of the same electrical charge). FIGS. 3A to 3E show reaction canals 2 of flow devices in which the different laminar polymer streams are joined together in different configurations. In the reaction canal 2, as depicted in FIG. 3A, the oppositely charged laminar polymer streams A and B are flowing side by side whereas in FIG. 3B they are flowing stacked one above the other through the reaction canal 2. In a further example illustrated in FIG. 3C, different kinds of laminar polymer streams of first (A and Z) and second charged polymer (B and C) are stacked one above the other. In FIG. 3D, a laminar polymer stream of a cell containing second charged polymer (B) is sandwiched between two laminar polymer streams of first charged polymers (A and Z) and in FIG. 3E, a laminar polymer stream of a first charged polymer (A) is surrounded by several laminar polymer streams of second charged polymers (B to I) which contain different cell species.

FIG. 10A shows a negative control with dead hepatocytes. FIG. 10B shows the view on an upstream portion of the canal (mid-slice from bottom). FIG. 10C shows the view on a downstream portion of the canal (mid-slice from bottom). By monitoring both ends of the reaction canal it is demonstrated that the cells are functional throughout the reaction canal. Hepatocytes embedded in the polymer matrix both in the upstream portion and downstream portion of the canal are highly fluorescent (cells in the left side pictures), indicating that hepatocytes showed functionally active cytochrome P450 activities.

FIGS. 11A, B and D: area between the upper pair of arrows shows the dense wall; area between the pair of arrows in the middle of the picture shows the dense fibers; area between the lower pair of arrows shows the loose fibers; FIG. 11 C: area between the upper pair of arrows shows the loose fibers; area between the pair of arrows in the middle of the picture shows the dense fibers; area between the lower pair of arrows shows the dense wall.

DETAILED DESCRIPTION OF THE INVENTION

Figure 1:
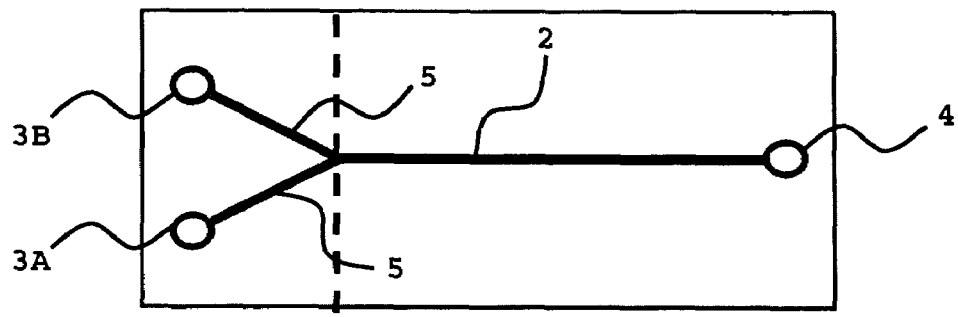
FIG. 1 shows a top view (FIG. 1A) and side view (FIG. 1B) of a flow device of an embodiment of the present invention. In this embodiment, the flow device has two inlet openings 3A and 3B and one outlet opening 4. The inlet openings 3 and the outlet opening 4 are connected to the (reaction) canal 2 of the flow device via inlet and outlet canals 5, respectively, wherein canals 5 of this embodiment are arranged perpendicular to the reaction canal 2, as can be seen in FIG. 1B.
Figure 1:
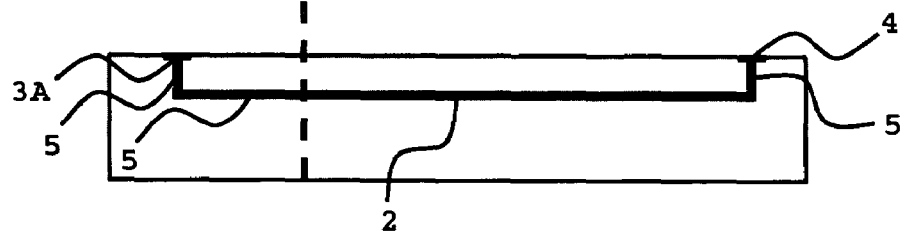

In the method of the present invention at least one cell species is immobilized in a matrix formed by biocompatible charged polymers. This method comprises:

providing a first charged polymer and a second charged polymer, wherein the at least one cell species is embedded in the second charged polymer and wherein the first charged polymer has an electrical charge opposite to that of the second polymer, and reacting the polymers under laminar flow conditions to form a matrix for the at least one cell species. This method allows for the first time to create matrix configurations for cells in which different cells are embedded in the same or different layers of the matrix that are arranged lying side by side in the same plane and/or are stacked one above the other.

This method enables creation of cell matrices for immobilizing cells under conditions that are comparable to the conditions provided by the extracellular matrix (ECM) structure of living tissue. With the term 'immobilizing' it is meant that the cells are embedded in a charged polymer that forms a matrix upon reaction with the oppositely charged polymer. The cells are then fixed within this polymer matrix but are still able to grow and therefore also to change their position, e.g. during cell division, within the structure provided by the matrix. Therefore, this method allows to grow any cell species that can be cultivated in vitro. It also allows to grow and study cell species that require a three-dimensional matrix and/or cell species which cannot be cultured with cell culture methods that are known in the state of the art, as for example growing of cells in petri-dishes or culture flasks. Also cell species which need to be co-cultured with other cell species can be grown using the method of the present invention.

In one example, an eukaroytic cell species is used, wherein this cell species may be a mammalian cell. The cells are mixed with the second charged polymer and the mixture is then reacted with the oppositely charged first polymer under laminar flow conditions to form a polymer matrix. Examples of mammalian cell species include, but are not limited to, primary hepatocytes, HepG2, bone marrow mesenchymal cells, fibroblasts, chondrocytes, Langerhans cells, cardiac myocytes, keratinocytes, oligodendrocytes, endothelial cells, epithelial cells, smooth muscle cells, lipocytes, neurons and osteoblasts. Other cell species that can be used in the method of the present invention can be selected from the group comprising or consisting of plant cells, yeasts, amphibian cells, insect cells and prokaryotic cells. The prokaryotic cells may be from, but are not limited to, the genus *Escherichia, Bacillus* or *Lactococcus*. Some examples of prokaryotic cells from these genera are *Escherichia coli, Bacillus subtilis* or *Lactococcus lactis*.

The matrix in which the above described cells are immobilized is formed upon reaction of the oppositely charged polymers in a (reaction) canal 2 of a flow device. The charged polymers that can be used in the method of the present invention react to a polymer complex which polymer complex forms a three dimensional polymer matrix that can be perfused by liquids and is permeable to substances necessary to sustain the normal metabolic functions of the at least one cell species and to products released by the at least one cell species. The polymer complex is formed upon reaction of the second charged polymer containing the at least one cell species with the first charged polymer, wherein the first charged polymer has a sufficient charge density to react with an oppositely charged second polymer to form a polymer complex at physiologic pH. It is assumed that the polymerisation reaction of the present invention is a typical example for a coacervation reaction in which in the contact area one charged polymer is accumulating whereby the other polymer is diluted. Due to that a thin polymer 'wall' is formed as indicated in FIGS. 4A and 4B. On the adjacent sides of this wall a voltage drop occurs that causes the formation of a polymer matrix in which the cells can grow. Thus the ECM like structure is mimicked. Since the reaction conditions of the coacervation reaction can be rather exactly controlled in the present invention, as will be shown further below, also an effective control of the structure and density of the three-dimensional polymer matrix can be achieved using the method of the present invention.

Figure 2:
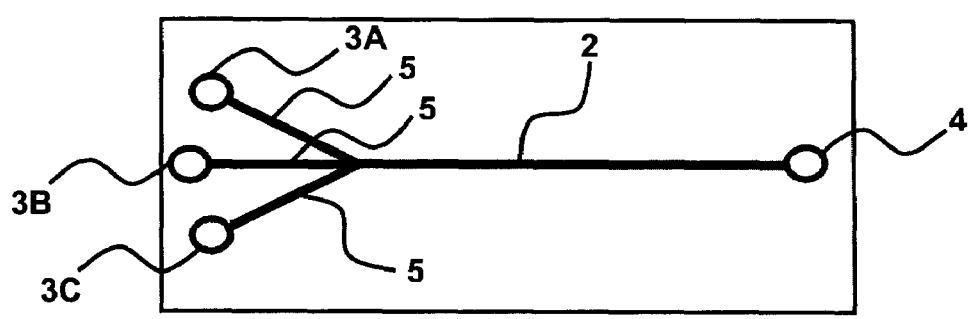
FIG. 2 shows perspective views of possible flow devices of the present invention in which the inlet openings 3 and the outlet opening(s) 4 are connected to the (reaction) canal 2 of the flow device via inlet and outlet canals 5, respectively.
Figure 2:
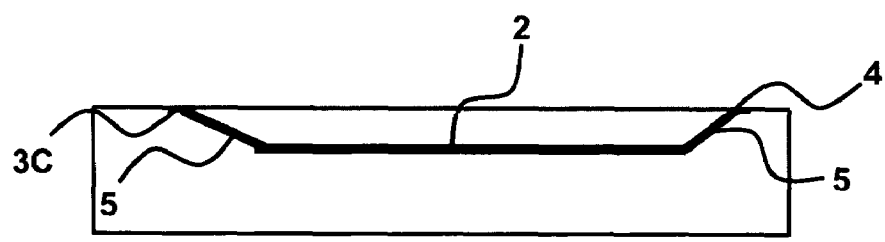
Figure 2:
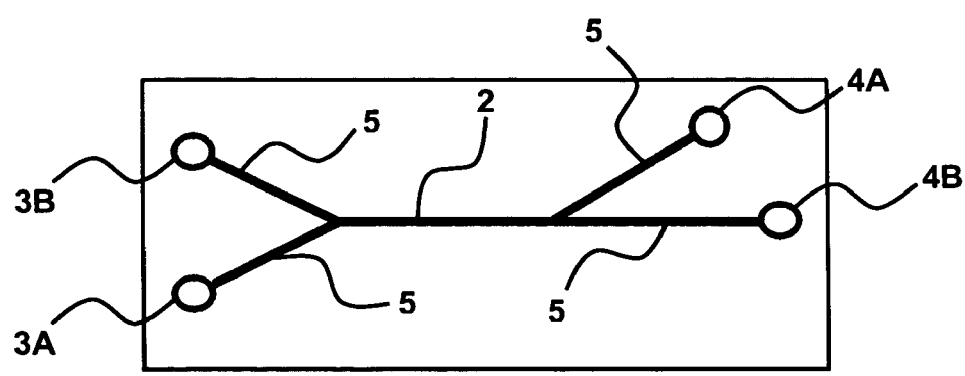
Figure 2:
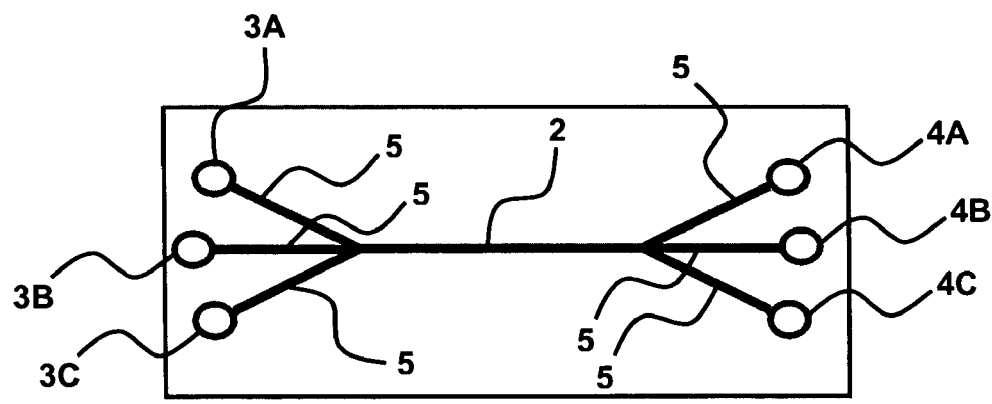

The coacervation reaction takes place in the reaction canal 2 of the flow device examples of which are shown in FIGS. 1 and 2. The laminar polymer streams are pumped into the canals of the flow device under laminar flow conditions. Pumping of the polymer streams can be performed with any device that allows the creation of laminar flows of liquid streams. Pumps that can be used in the method of the present invention may be positive-displacement reciprocating pumps or metering syringe pumps, to name only two. If possible laminar flow conditions can be achieved without any special device simply by adjusting the diameter of the canals to control the amount of different polymers flowing through the device by gravity force.

The polymerisation reaction of the oppositely charged polymers takes place once the laminar polymer streams get into contact with each other. For the formation of the polymer complex and thus the three-dimensional polymer matrix, it is necessary to slow down the laminar polymer streams for sufficient diffusion to allow the polymerisation reaction to finalize. Using the coacervation reaction of oppositely charged polymers, a three-dimensional polymer matrix is formed within 2 to 8 minutes after contact of the oppositely charged laminar polymer streams. In the method described by Wei Tan, M. S. and T. A. Desai (Tissue Engineering, 2003, Vol. 9, No. 2, P. 255-267) it takes more than 15 min. until the polymer matrix is formed between two polymers that have been layered on top of each other. In the experiment described by Wei-Tan and Desai, native collagen or a mixture of collagen and chitosan was used. The time frame for the formation of the polymer matrix is important because fast formation of a polymer matrix allows an earlier perfusion of the matrix with fresh media which avoids dehydration of the newly formed polymer matrix. Thus, the viability rate of the embedded cell species is increased.

By diluting the charged polymers which have not reacted to form a polymer complex with a suitable liquid media, the polymerisation reaction is stopped. This "stop solution" can be, e.g., phosphate buffered saline (PBS), a cell culture media or any other liquid media that is not toxic to the cells embedded in the newly formed polymer matrix. For example, the polymerisation reaction of a terpolymer composed of hydroxyethyl methacrylate, methacrylic acid and methyl methacrylate (HEMA-MM-MMA) with methylated collagen as described in Example 1 can be stopped using Phosphate Buffered Saline (PBS, pH 7.0), Dulbecco's Modified Eagle Medium (DMEM) or modified Chee's medium (HeptaoZYM-Serum Free Media from Gibco BRL). Besides replacing one of the laminar polymer streams with a stop solution, it is also possible to pump the laminar polymer streams into the flow device through the inlet openings 3 and to pump the stop solution into the reaction canal 2 through the outlet opening(s) 4 on the opposite side of the flow device (see for example FIG. 2B). Thus, the reaction canal 2 is half-filled with parallel laminar polymer streams and half-filled with a stop solution to stop the polymerisation reaction after 2 to 8 minutes. The effective perfusion of the polymer matrix formed upon reaction of the oppositely charged polymer streams with an analyte containing liquid media is illustrated in Example 2. Example 2 describes metabolization of 7-ethoxyresorufin by hepatocytes embedded in a polymer matrix that was pumped into the reaction canal 2 that contains the polymer matrix.

Once the three-dimensional polymer matrix is fully developed the cell species embedded in this polymer matrix can be grown or exposed to different solutions that contain different kind of analytes as described in Examples 2 and 3, for instance.

One advantage of the present invention is the formation of a physically stable three-dimensional polymer matrix in form of a 'polymer strip'. Due to the excellent stability of this polymer strip, it can be peeled out of the flow device using for example the method as described by W. Tan and T. A. Desai (Biomaterials, 2004, Vol. 25, P. 1355-1364). After peeling the polymer strip out of the canal, the polymer strip can be fixed on biochips for imaging and biological studies or be used in biosensors and bioreactors, to name only a few options. To achieve an even more stable polymer strip a configuration of laminar polymer streams as illustrated in FIG. 3D and described in more detail further below can be used in which the laminar stream of a cell containing second charged polymer is sandwiched between two laminar streams of a first charged polymer.

Examples of flow devices that can be used for the method of the present invention are shown in FIGS. 1 and 2. A suitable flow device typically comprises two or more inlet openings 3 that are fluidly connected to the reaction canal 2, for example, via canals 5 to allow laminar polymer streams to flow into the reaction canal 2. In addition such a flow device usually further comprises one or more outlet opening(s) 4 that are fluidly connected via perpendicularly or transversely orientated canals 5 to the reaction canal 2. The arrangement and number of canals 5 and openings 3, 4 that lead to or away from the reaction canal 2 depends on the desired configuration of the laminar polymer streams that polymerize to form the three-dimensional polymer matrix within the reaction canal 2.

Examples for different configurations of laminar polymer flows are shown in FIG. 3. If one or more cell species are to be embedded in the same second charged polymer the laminar polymer streams might be arranged as depicted in FIGS. 3A and 3B. For this configuration of laminar polymer streams, a flow device with inlet and outlet openings positioned as shown in FIG. 1A might be used. Described in more detail, in FIG. 3A a laminar polymer stream of a first charged polymer (A) flows side by side to a laminar polymer stream of a second charged polymer (B), whereas in FIG. 3B the two polymer streams (A) and (B) are stacked on top of each other. Once the reaction canal is filled to the desired length of the later formed polymer strip, the first and second charged polymer polymerize to form the three dimensional polymer matrix embedding the cells.

An arrangement of canals as shown in FIG. 1A is advantageous, if further experiments and tests are to be carried out directly within the canal of the flow device. The use of a flow device as depicted in FIGS. 2A and 2D, allows an arrangement of different laminar polymer streams as depicted in FIG. 3D. In this configuration, the laminar polymer stream of a second charged polymer (B) containing the cells is sandwiched between two laminar polymer streams of first charged polymers A and Z, wherein the laminar polymer streams of first charged polymers A and Z can contain the same or different first charged polymers depending on the desired form of the polymer matrix formed. This sandwich arrangement enables the production of an even more stabilized polymer strip compared to a configuration as depicted in FIGS. 3A or 3B. This might be advantageous if the polymer strip is peeled off the polymer device to be used, e.g., for biochips on which the cell containing gel strip is fixed for further use. Furthermore, a flow device of FIG. 2D allows a greater flexibility and a better control as a flow device as depicted in FIG. 2A. For example, more outlet openings allow to suck the laminar polymer streams separately from each of the outlet canals which allows a better control of the flow rate of the different charged polymers.

On the other hand, if cell species with different requirements with respect to the polymer matrix are used, an arrangement of different laminar polymer streams as depicted in FIG. 3C might be advantageous. Different laminar polymer streams of second charged polymers (B) and (C) embedding the cells and laminar polymer streams of first charged polymers (A) and (Z) can be used to form suitable three dimensional cell matrices upon reaction of the oppositely charged polymers in the reaction canal of a flow device that comprise at least four input openings (not shown). Since the three dimensional polymer matrices formed can be perfused by liquids and are permeable to metabolic substances, such configurations allow the cells to exchange metabolic substances with each other. This embodiment is especially suitable for cell species that can only grow in co-cultures of different cell types. A co-culture can maintain the differentiated phenotype of many highly differentiated cells for longer periods of time, e.g. sinusoidal endothelial cells (DeLeve L. D. et al., Am J Physiol Gastrointest. Liver Physiol., 2004 Jun. 10), hepatocytes (Harimoto M., et al., J. Biomed. Mater. Res., 2002, Vol. 62(3), P. 464470) or clonal C2C12 myotubes (Cooper S. T. et al., Cell Motil. Cytoskeleton, 2004, Vol. 58(3), P. 200-211). The co-culture of embryonic stem cells or other progenitor cells with other cell types can direct their differentiation (Wang XY, et al., Surgery, 2003, Vol. 134(2), P. 189-196; Fair J. H., Brain Res. Dev. Brain. Res., 2002, Vol. 137(2), P. 115-125).

An arrangement of laminar polymer streams in a reaction canal of a flow device (not shown) as depicted in FIG. 3E might be advantageous if several cell species are to be tested at the same time with different analytes that will be perfused through the permeable polymer matrix. In the embodiment as depicted in FIG. 3E a laminar polymer stream of a first charged polymer (A) is in contact with several laminar polymer streams of second charged polymers (B)-(I). Each laminar polymer stream of these second charged polymers (B)-(I) contains at least one cell species. The above examples illustrate one further advantage of the present invention, namely to create different polymer matrix configurations that can be easily and fast composed according to the requirements of the cell species used. Side by side flows of laminar polymer streams are possible as well as configurations in which different layers of laminar polymer streams are stacked one above the other. Configurations in which the laminar polymer streams are stacked one above the other (e.g. FIG. 3B to 3E) are of special interest as they allow to mimic the ECM structure in living tissue in more detail.

Both, naturally occurring and modified polymers are suitable for use as charged polymers in the practice of the present invention. In this connection it is noted that the term "electrically charged" means that the polymers carry a net charge, i.e., are either positively or negatively charged, when present in a solution. Accordingly, the term that "two polymers are of the same electrical charge" means that they both carry an either positive or negative net charge the exact value of which (expressed for example in Coulomb) can be different. Thus, the term "of the same electrical charge" has to be understood qualitatively and not quantitatively.

The polymers used in the present invention are typically water soluble and biodegradable and in addition usually have a molecular weight of at least 10 kDa. It is possible that the first charged polymer as used herein is negatively charged. In such a case, the second charged polymer is of course positively charged. Alternatively, the first charged polymer is positively charged and the second charged polymer carries a negative net charge.

Polymers that are suitable for the use in the present invention include chitosan, polyanionic alginate, positively charged collagen, negatively charged collagen polyanionic alginate, $Ca^{2+}$, or synthetic polymers such as polycationic poly(L-lysine) and co-polymers or terpolymers that include poly(acrylic acid), poly(methacrylic acid), poly(methacrylate) or poly(methyl acrylate) to name only a few.

A useful terpolymer may consist of two polymer blocks containing at least one of acrylic acid and methacrylic acid and at least one of hydroxyethyl methacrylate and hydroxylpropyl methacrylate. Such terpolymers may consist of about 10%-50% hydroxyethyl methacrylate, about 10%-50% methacrylic acid and about 50% methyl methacrylate (HEMA-MM-MMA). An example for such a terpolymer consists of 25% hydroxyethyl methacrylate, about 25% methacrylic acid and about 50% methyl methacrylate (HEMA-MM-MMA) (Chia et al., Tissue Engineering 2000 Vol. 6(5), P. 481-495). In another example, the terpolymer consists of 25% hydroxyethyl methacrylate, about 50% methacrylic acid and about 25% methyl methacrylate (HEMA-MM-MMA).

Other terpolymers that can be used in the method of the present invention are described by Shao Wen et al who used terpolymers of different compositions for embedding living cells (Shao Wen, Yin Xiaonan and W. T. K. Stevenson, Biomaterials, 1991, Vol. 12 May, P. 374-384; Shao Wen, H. Alexander et al., Biomaterials, 1995, Vol. 16, P. 325-335). These terpolymers consist of HEMA-MMA-MM or HEMA-MMA-DMAEMA (cationic 2-(dimethylamino)ethyl methacrylate) whereas the latter terpolymer is positively charged.

Combinations of polymers from this group can be used to form a polymer matrix for embedding living cells by coacervation. Exemplary combinations of polymers in which the first charged polymer are reacted with the second charged polymer include the following (wherein the second charged polymer is mentioned first, followed by the first charged polymer): chitosan—negatively charged terpolymer, polyanionic alginate—$Ca^{2+}$, positively charged collagen—negatively charged terpolymer, negatively charged collagen—positively charged terpolymer (Shao Wen, Yin Xiaonan and W. T. K. Stevenson, Biomaterials, 1991, Vol. 12 May, P. 374-384), polyanionic alginate—polycationic poly(L-lysine).

If more than two layers of charged polymer are stacked one above the other (see FIG. 3C) within the reaction canal 2, different kinds of polymers can be used. Not only a combination like alternating layers of terpolymer and collagen can be stacked one above the other but also collagen and terpolymer followed by chitosan and then again a layer of terpolymer followed again by collagen or chitosan. For the coacervation reaction it is important that two oppositely charged polymers are stacked one above the other which can form a suitable polymer matrix for the cells embedded therein. Another factor influencing the choice of the polymer is the cell species to be embedded. Depending on the cell species a suitable biocompatible polymer for this cell species has to be chosen. Also the polymers that are reacting with another should ideally provide a structure of the polymer matrix that is suitable for the cell species used to grow therein. Suitable polymers are mentioned above.

Since polymers such as collagen are in their natural form neither positively nor negatively charged they need to be modified for use in the present invention. Techniques to modify such polymers are known in the state of the art. In Chia et al. for example (Tissue Engineering, 2000, Vol. 6(5), P. 481-495) cationic collagen was obtained by esterification of the carboxyl groups with low-molecular-weight alcohol. Negatively charged collagen can, for example, be obtained by the method described by Donald G. Wallace and Joel Rosenblatt (Advanced Drug Delivery Reviews 2003, Vol. 55, P. 1631-1649). Other examples of an uncharged polymer that can be modified to carry an electrical net charge include, but are not limited to poly (vinyl alcohol) and further polysaccharides such as dextrans and polysaccharides of the carrageenan family (obtained from the red seaweeds).

Optionally, polymers that are naturally charged can be modified to (better) match the electrical charge of the oppositely charged polymer that is used as reaction partner. The different electrical charge can also be used to influence the permeability of the polymer matrix. Large differences in charge densities between the oppositely charged polymers tend to make the membrane more permeable.

As the polymerisation isolates the cells physically from the culture media that they need to survive, it is necessary for the cells that the membrane formed by the polymer complex is permeable to nutrients that are imperative for the survival of the embedded cells. It is also necessary to allow other liquids to penetrate the matrix if the polymer matrix obtained by the method of the present invention is used, e.g., as test matrix for toxic substances. As can be seen from Example 2 the polymer matrix of the present invention is penetrable for liquid media which transport metabolites necessary for the survival of the cells embedded within the three dimensional polymer matrix.

The method of the present invention allows to compose ECM like matrices whereby these matrices is formed by complex coacervation of charged polymers within the reaction canal 2. This complex coacervation can be effectively controlled using the method of the present invention. By varying the molecular weight, the charge density and the concentration of the charged polymers as well as the reaction time of the oppositely charged polymers within the reaction canal, the permeability and transport properties of the membrane can be modulated depending on the requirement of the cell species embedded therein.

The influence of different charge densities on the formation of the polymer matrix and their respective effect on the functionality of the embedded cells is demonstrated by modulating the charge density of collagen that is used as second charged polymer. Using the method described by Chia et al. (Tissue Engineering 2000, Vol. 6, P. 481-495) type I bovine dermal collagen (Vitrogen, Cohesion Technologies Inc., Palo Alto, Calif.) is modified to be cationic via methylation.

The degree of methylation is controlled by adjusting the reaction time and temperature of a polymer as described in Example 3. The methylation degree is determined using a capillary zone electrophoresis method that was developed by the inventors and is described in Example 3. Using this new method a CE index is proposed by the inventors to monitor the degree of methylation of a polymer used in the method of the present invention. An increase in polymer methylation is correlated with an increase in this CE index. For example, a slightly methylated polymer has a CE index of about between 0.9 and about 1.7 whereas a highly methylated polymer has a CE index of about between 1.7 and about 2.5.

Figure 5:
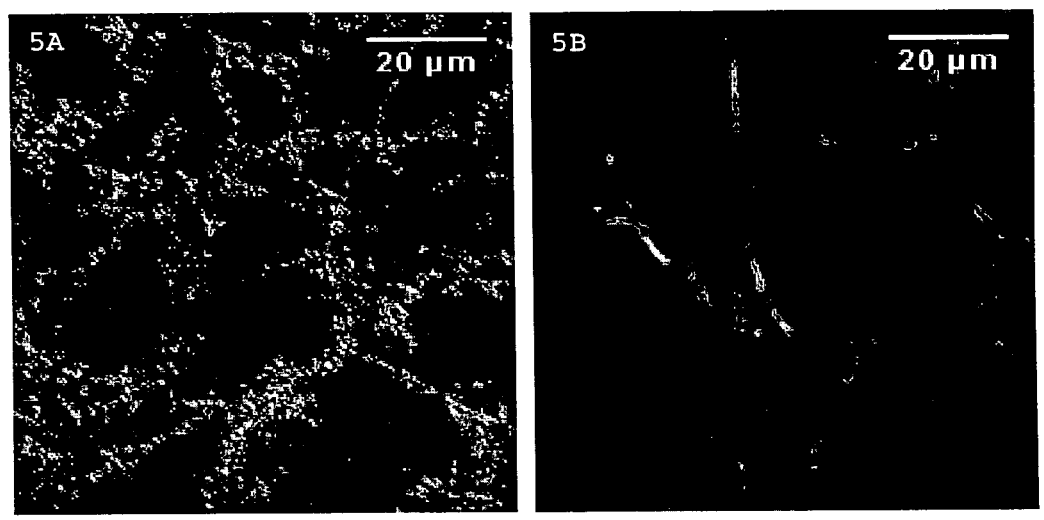
FIG. 5 illustrates the effect of different kinds of collagen methylation on polymer matrix formation (see Example 3). Representative images of collagen matrices formed with 3 wt % terpolymer: (A) Slightly methylated collagen (CE index 1.4); (B) Highly methylated collagen (CE index between 1.9).

When slightly methylated collagen (CE index 1.4) is used to react with a first charged polymer, e.g. HEMA-MMA-MM, the matrix formed upon reaction of the polymers consists of more cross linked and thicker fibers as can be seen from FIG. 5A. On the other hand using highly methylated collagen (CE index 1.9) leads to lesser cross linked and thinner fibers (see FIG. 5B). Therefore, an increase in collagen methylation can be correlated with more fragmented matrix morphology as can also be seen from FIGS. 6A and 6B which compare the mean dendritic length and number formed by slightly and highly methylated collagen.

Figure 8:
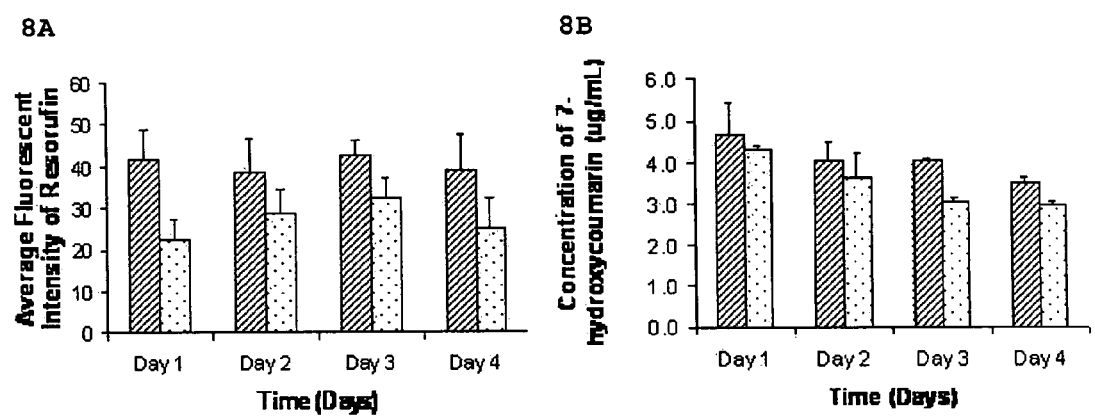
FIG. 8 illustrates the effect of collagen methylation on hepatocyte detoxification cytochrome P450-dependent monooxygenase activities (see Example 3). (A) 7-ethoxyresorufin-O-dealkylation (EROD) activity, as quantified by the average fluorescent intensity of resorufin; (B) 7-ethyoxycoumarin-O-deethylase (ECOD) activity, as quantified by the concentration of 7-hydroxycoumarin. [(●) Slightly methylated collagen; (○) Highly methylated collagen].

The polymer matrix formed by different methylated collagen influences the functionality of the cells embedded therein. As described in Example 3, detoxification functions of primary hepatocytes are influenced depending on whether they are embedded in slightly (CE index 1.4) or highly (CE index 1.9) methylated collagen. The detoxification activity of primary hepatocytes was higher when slightly methylated collagen was used to form the polymer matrix (FIGS. 8A and 8B). In contrast, amplification of HepG2 cells was greater in highly methylated collagen than in slightly methylated collagen.

Therefore, the proposed method of controlling the formation of the polymer complex by influencing the charge density on a polymer was demonstrated to be capable of modulating the matrix morphology to provide differential levels of cellular support. In particular, the precise control of the polymer matrix supporting live cells is important in cellular support and functions because the cell functions were selectively augmented in matrices with different fiber cross linking.

Another example as how to influence the structure of the polymer matrix is to alter the molecular weight of the polymers and their concentration. In one experiment HEMA-MAA-MMA as first charged polymer and positively charged (methylated) collagen as second charged polymer have been used to form the polymer matrix (Example 1). The structure of the polymer matrix was altered by using terpolymer HEMA-MM-MMA of different molecular weight and concentration. The polymer matrix formed by HEMA-MM-MMA of low molecular weight and high concentration (3 wt %) is more reticulated and wide meshed (FIGS. 4A, C, E and F) than a polymer matrix formed with HEMA-MM-MMA of high molecular weight (FIGS. 4B and D) and low concentration (0,1 wt %).

Another option to influence the reaction conditions for the method of the present invention is to vary the reaction time of the oppositely charge polymers. This can be done by altering the static reaction time or the dynamic reaction time. The dynamic reaction time means the contact time of the oppositely charged polymers while they flow in contact with each other through the reaction canal. The static reaction time means the contact time of the oppositely charged polymers within the canal when they have stopped flowing through the canal. As described in Example 4, polymer matrices formed under reaction time conditions in which the static time is increased compared to the dynamic reaction time, such polymer matrix formed greater amounts of loose fibers and a cross-sectionally more uniform fiber matrix (see FIG. 11).

Flow simulations with laminar polymer streams of different viscosity have shown that as more viscous one stream is than the other, the more the boundary between the laminar polymer streams is pushed to the less viscous side. The structure of the polymer matrix formed can also be influenced by controlling the reaction time of the oppositely charged polymers within the reaction canal, as can be seen from Example 1, 2 and especially 4. In typical embodiments, the reaction time of the charged polymers is normally between about 30 sec to about 8 min, but also longer reaction times, for example, up to 30 minutes are possible. The appropriate reaction time can be determined empirically and the determination is well within the knowledge of the person skilled in the art.

The flow device that can be used together with the method of the present invention can be made from any material that is biocompatible. Biocompatible materials include, but are not limited to, glass, silicon, certain types of metal and a polymerisable material. The polymerisable material includes, but is not limited to, monomers or oligomeric building blocks (i.e. every suitable precursor molecule) of polycarbonate, polyacrylic, polyoxymethylene, polyamide, polybutylenterephthalate, polystyrene, polyphenylenether, polydimethylsiloxane (PDMS), mylar, polyurethane, polyvinylidene fluoride (PVDF), flourosilicone or combinations and mixtures thereof. In some embodiments, the biocompatible material comprises PVDF and/or PDMS. Advantages of PVDF and PDMS are their cheap price and superior biocompatibility. In addition, they have high gas permeability, a characteristic which is important in closed microdevices as it facilitates the permeation of supplied oxygen to the cell culture in order to ensure cell respiration. Furthermore, as they are transparent, they conveniently allow direct morphological observation of the cells to be carried out under an observation device, e.g. a microscope.

The canals 5, 2 of a flow device used in the method of the present invention can be of any shape and dimension as long as they are suitable of allowing laminar flows of the laminar polymers streams to be contacted with each other. A canal can have, e.g., a rectangular, other polygonal or a round shape. The dimensions of a rectangular canal can be, but are not limited to, of between 10 to 800 µm in width and of between 10 to 600 µm in height. The length of the reaction canal depends on the use of the polymer strip formed therein. Typically, the reaction canal has a length of about 0.4 µm to about 6 cm but is not limited to this length.

The flow conditions (laminar or turbulent flow) of streams of charged polymers depend on the dimensionless Reynolds Number (Re) and depend on the density and viscosity of the polymers used.

$$Re = \frac{\text{(fluid density)(mean fluid velocity)(characteristic liquid)}}{\text{fluid dynamic viscosity}}$$

"Laminar flow conditions" are given, if the Reynolds number has a value of less than 2000 and thus can be readily determined. The use of laminar flow conditions for simulating in vivo conditions is described by Takayama et al. (Proc. Natl. Aca. Sci., May 1999, Vol. 96, P. 5545-5548). In this study laminar flows of liquid media were used to simulate the patterning of the cell culture substrate. In the method of the present invention laminar polymer streams instead of liquids are used to pattern a three dimensional matrix and cells together at the same time.

In one experiment using the method of the present invention a flow device (see FIG. 1A together with FIG. 3A) was used that was prepared as described in Example 1. The rectangular reaction canal of this flow device had a length of about 3.5 cm a height of about 200 µm and a width of about 400 µm. Positively charged collagen was used as second charged polymer (B) and a negatively charged HEMA-MMA-MM terpolymer as described in Example 1 was used as first charged polymer (A). The two polymer streams flow in a side by side configuration as can be seen in FIG. 3A. The laminar flow conditions that can be used for such a configuration are described in Table 1.

The average viscosity of the polymer used for the method of the present invention is usually between about 0.003 kg/m*s to 0.009 kg/m*s and the density of the polymers is between about 997 kg/m$^3$. Using the dimensions of the canals and the polymers as characterized in the present invention, the Reynold number in such canals is typically low and fulfills the requirements for creating laminar flows. In the system described in Table 1 for example, the Re is <4 for both polymer streams.

TABLE 1

Calculations for collagen and terpolymer side by side flows (FIG. 3A) in the following configuration:

| | positively charged collagen (B) | negatively charged terpolymer (A) |
|---|---|---|
| Volume Flow Rates (µl/h) | 1000 | 1000 |
| Volume Flow Rates (m$^3$/s) | 2.77 * 10$^{-09}$ | 2.77 * 10$^{-09}$ |
| Fluid Density (kg/m$^3$) | 997 | 997 |
| Fluid Dynamic Viscosity (kg/m * s) | 0.007 | 0.004 |
| Hydraulic diameter (m) | 0.0004 | 0.0004 |
| Mean Velocity (m/s) - One side | 0.069 | 0.0347 |
| Re - each stream | 3.83 | 2.89 |

Another aspect of the present invention is the use of the method of the present invention to immobilize cells in matrices formed by biocompatible charged polymers, to generate microsized implantable tissues, to generate in vitro models of physiological tissues and to generate bioreactors which can be used to perfuse cell cultures for the manufacture of recombinant proteins in biotechnology. The method of the present invention can also be used for cell amplification in tissue engineering, the manufacture and control of stem cell differentiation for therapeutic uses, for cell biochips which can be used for imaging and biological studies, e.g., perfusion co-cultures to study heterotypic cell-cell interactions, perfusion cultures to study effect of shear forces, growth factor gradients and oxygen gradients on cellular behaviour, and for cell biochips for ADME/Tox, High Throughput Screening (HTS), biosensors and cancer diagnostics. The microsized implantable tissues can also be used as micropatterned scaffolds with cells such as osteoblasts for bone grafts and islets for pancreatic islet transplantation.

EXAMPLE 1

Example 1 illustrates the in situ formation of a polymer matrix by laminar reaction of methylated (positively charged) collagen as second charged polymer and (negatively charged) terpolymer of hydroxylethyl methacrylate-methyl methacrylate-methyl acrylic acid (HEMA-MMA-MM) as first charged polymer under laminar flow conditions.

In this example, two different combinations of this polymer are used that are composed of different concentrations of collagen and terpolymer of different molecular weight. The formation of a polymer matrix is based on the polyelectrolyte complex coacervation between cationic methylated collagen and anionic terpolymer of HEMA-MMA-MM. This polymer matrix has been shown to provide favorable three dimensional microenvironment for cell support and proliferation (Chia et al., Tissue Engineering 2000, Vol. 6(5), P. 481-495). Two different polymer combinations are used to illustrate the control of the structure of the polymer matrix formed using different polymer combinations. The two combinations are chosen based on the optimal charge balance between the two polyelectrolytes.

Type I Bovine dermal collagen (Vitrogen, Cohesion Technologies Inc., Palo Alto, Calif.) is modified to be cationic via esterification of the carboxyl groups on collagen chains as described by Chia et al. (2000, supra). Terpolymer of HEMA-MMA-MM is synthesized by solution polymerization at feed ratios of HEMA, MMA and MAA at 25:50:25 according to Chia et al. (2000, supra). Gel Permeation Chromatography is used to characterize the molecular weights (MW) of the two terpolymers. These were found to be 80.5 kDA for the low MW and 849.3 kDa for the high MW. Both collagen and terpolymer solutions are reconstituted in 1× Phosphate Buffered Solution (PBS) to their respective concentrations. The two polymer combinations are as follows:
  (i) 3 mg/ml methylated collagen and 3 wt % low MW terpolymer,
  (ii) 3 mg/ml methylated collagen and 0.1 wt % high MW terpolymer.

The reaction canal of the device as shown in FIG. 1 is fabricated with poly(dimethylsiloxane) (PDMS) elastomer because of its ease of rapid prototyping. The design of the canal is made by a computer-aided design (AutoCAD) program and used to make the master for fabricating PDMS molds by Computer Numerical Control (CNC) machining in polycarbonate. A variety of other methods can be used to produce the master for fabricating the PDMS structures such as use of the photocurable epoxy SU-8 (Tan W. and Desai T. A., Tissue Engineering 2003, Vol. 9(2), P. 255-267); other techniques can also be used for fabricating the canals such as etching in glass or silicon (McDonald et al., Electrophoresis 2000, Vol. 21(1), P. 27-40) as long as they allow parallel matrix polymers to contact in a laminar fashion (Re <2000). Under typical microfluidic conditions of small canals (up to 200 μm) and low flow rates (between 50-1000 μl/h), Re is almost always low. In this exemplary system Re is <2. To create the PDMS mold, a liquid PDMS prepolymer (in a mixture of 1:10 base polymer:curing agent) is poured onto the master and cured at 60° C. for 1 h. Small holes are drilled into the PDMS using a borer to produce inlets and outlets. Finally, the PDMS is sealed irreversibly on glass cover slips by plasma oxidation to form the canal. In this experiment, the rectangular reaction canal has a length of about 3.5 cm a height of about 200 μm and a width of about 400 μm.

Methylated collagen (top stream) and terpolymer (bottom stream) are delivered into the reaction canal 2 via the inlet openings 3A and 3B in FIG. 1A in the two Y arms using syringe pumps (KD Scientific Single-Syringe Infusion Pump from Fisher Scientific) with controlled flow rates (see Table 2). The merged laminar polymer stream is allowed to exit via the outlet opening 4 into the atmosphere at the end of the canal 5 (see FIG. 1B). After the formation of the polymer matrix on the collagen side, the terpolymer side is flushed and perfused with PBS. A variety of methods are used to characterize the polymer matrix formed, including light microscopy, confocal backscattering microscopy using 60× water lens and scanning electron microscopy (SEM).

Figure 4:
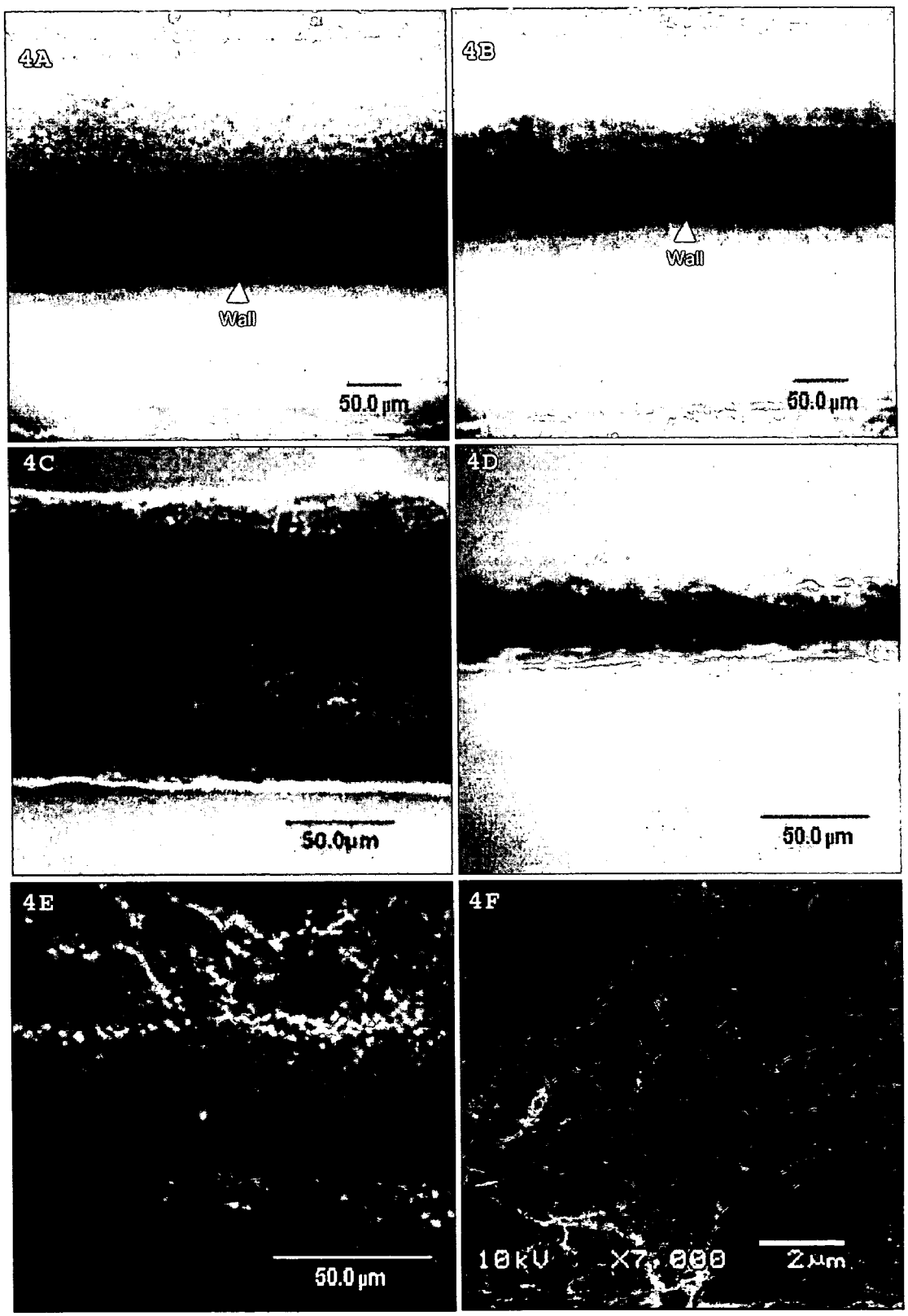
FIG. 4 shows the wall and polymer matrix formed after the methylated (positively charged) collagen as first charged polymer (top stream) and terpolymer (HEMA-MMA-MM) as second charged polymer (bottom stream) have been reacted and terpolymer side flushed with PBS after 8 mins. to stop the coacervation reaction (Example 1). Transmitted light micrographs showing the wall and collagen gel formed: (A) with 3 mg/ml methylated collagen and 3 wt % low MW terpolymer; (B) with 3 mg/ml and 0.1 wt % high MW terpolymer. Confocal backscattering images at mid-points along the canal, 50 µm from glass bottom: (C) 3 mg/ml methylated collagen and 3 wt % low MW terpolymer; (D) 3 mg/ml and 0.1 wt % high MW terpolymer; (E) 1.5× optical zoom on polymer matrix formed with 3 mg/ml methylated collagen and 3 wt % low MW terpolymer. (F) SEM micrographs of collagen matrix formed with 3 mg/ml methylated collagen and 3 wt % low MW terpolymer, which matrix forms the ECM like structure providing support for the different cell species.

For both polymer combinations (i) and (ii), a wall between the two charged polymers is formed upon contact of the two laminar polymer flows (streams). For configuration (i), as both laminar polymer streams were slowed down and the laminar collagen stream gradually reduced to 100 μl/h and then to zero, the polymer matrix is formed and filled up the collagen side of the canal (FIGS. 4A, 4C, 4E and 4F). More details with respect to the volumetric flow rates are given in Table 2. However for configuration (ii), after a thick and dense wall (indicated by the white arrow in FIG. 4) is formed, there is minimal coacervation on the side of the laminar collagen flow (FIGS. 4B, 4D). This is due to the greater chain entanglement effect for the longer chains of the higher MW terpolymer that limits further interaction of the charged polymers upon complexing (Wen S., et al., Biomaterials 1991, Vol. 12, P. 479-488). The wall and polymer matrix are retained after the terpolymer side is flushed with PBS after 8 minutes to stop the coacervation reaction, allowing the polymer matrix to be continuously perfused with liquids.

TABLE 2

Volumetric flow rates of methylated collagen and terpolymer with respect to time for matrix formation

| Methylated collagen-cell suspension flow rate in μl/h | Terpolymer flow rate in μl/h | Time in minutes |
|---|---|---|
| 500 | 500 | 2 |
| 250 | 250 | 2 |
| 100 | 100 | 2 |
| 0 | 100 | 2 |

The method of flowing oppositely charged polymers laminarly is an efficient means of forming polymer matrix micropatterns rapidly in situ without long times for coacervation of 15-20 minutes required by flowing in native collagen or solutions of native collagen and chitosan (Tan W. and Desai T. A. 2003, supra), and under mild and aqueous conditions that is non-toxic to cells.

The example also shows that the resulting polymer matrix micropattern formed can be manipulated by the use of different polymer combinations. The polymer matrix also retained its structural integrity after the terpolymer is flushed with PBS to stop the coacervation reaction. This demonstrates the potential of dynamically perfusing the cell-matrix micropatterns with media for the support of cell viability and functions.

EXAMPLE 2

This example shows the ability of the three dimensional polymer matrix to be perfused with analyte containing liquid media. For this purpose, detoxification functions of hepatocytes embedded in a polymer matrix formed by laminar side-by-side flows (as schematically shown in FIG. 3A) of methylated collagen and terpolymer of hydroxylethyl methacrylate-methyl methacrylate-methyl acrylic acid (HEMA-MMA-MAA) were studied.

For this experiment, freshly isolated primary rat hepatocytes were suspended in methylated collagen, and the cell-containing methylated laminar collagen stream was complex coacervated with an adjacent laminar stream of terpolymer. The hepatocytes embedded in the formed polymer matrix were cultured for 24 h and the hepatocytes detoxification functions assessed by their 7-ethoxyresorufin O-dealkylation (EROD) activities. The methylated collagen and the terpolymer HEMA-MMA-MAA used in this experiment were obtained as described in Example 1. Also the PDMS microchannel was fabricated as described in Example 1. Freshly isolated hepatocytes were suspended in methylated collagen at a density of $3 \times 10^6$/ml. The flow rates for the cell-containing methylated collagen and terpolymer streams are given in Table 3.

TABLE 3

Volumetric flow rates of methylated collagen and terpolymer with respect to time for matrix formation

| Methylated collagen-cell suspension flow rate in μl/h | Terpolymer flow rate in μl/h | Time in minutes |
|---|---|---|
| 1000 | 1000 | 2 |
| 100 | 100 | 1 |
| 50 | 100 | 1 |
| 0 | 0 | 4 |

After the formation of the polymer matrix using the flow rates indicated in Table 3, the terpolymer stream was replaced with HepatoZYM-Serum Free Media (GIBCO Laboratories) to be perfused at 200 μl/h for hepatocyte culture.

Figure 10:
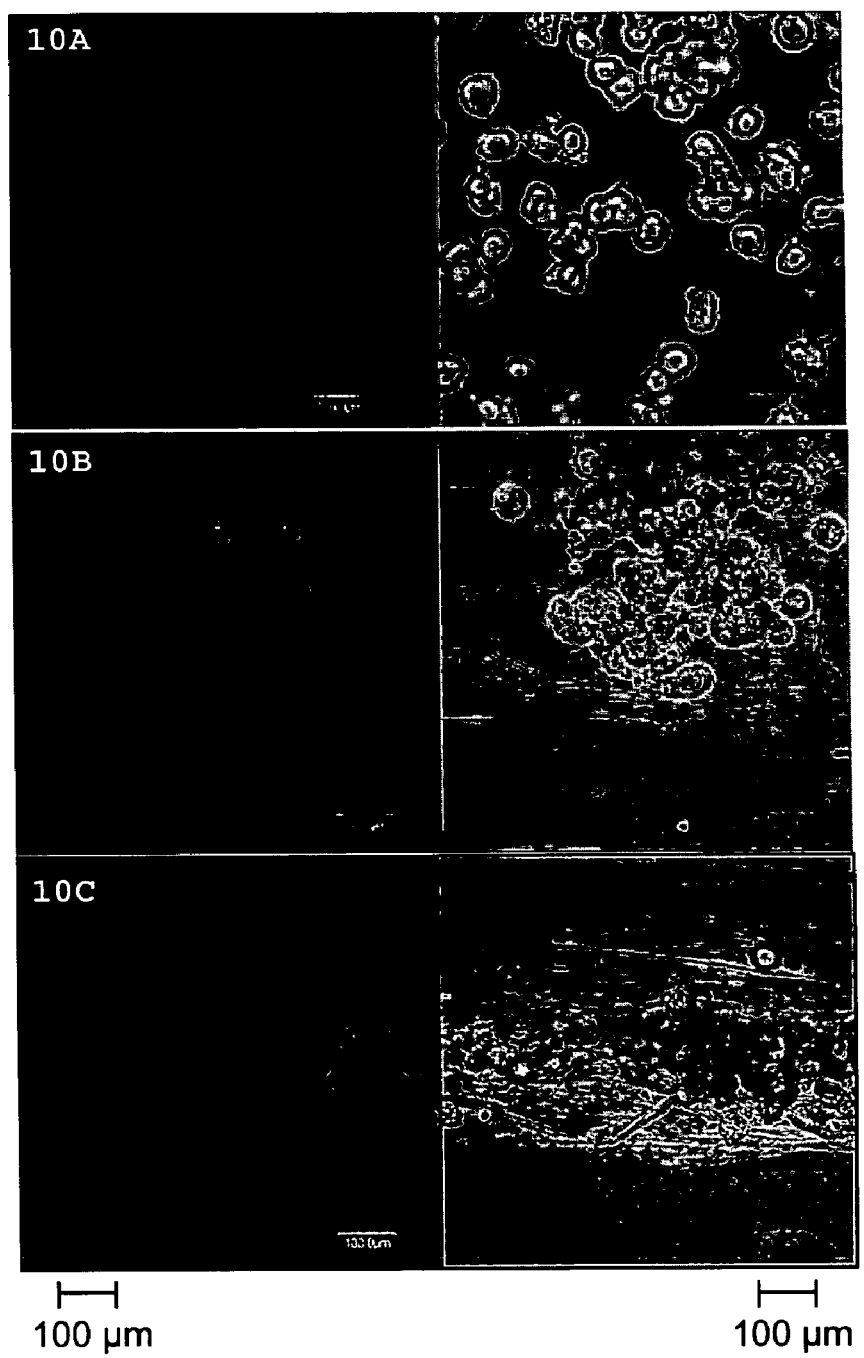
FIG. 10 shows confocal micrographs of embedded hepatocytes after 4h incubation in 39.2 µM 7-ethoxyresorufin in HepatoZYM-Serum Free Media demonstrating the perfusion of analyte containing liquids in the three-dimensional polymer matrix (Example 2).

The hepatocytes detoxification functions were assessed after 24h by the 7-ethoxyresorufin O-dealkylation (EROD) activity of hepatocytes. Briefly, these involved the perfusion of 39.2 μM 7-ethoxyresorufin in HepatoZYM-Serum Free Media for 4h and the quantification of their metabolic product, the highly fluorescent resorufin, by confocal fluorescent microscopy (Olympus Fluoview 300). For the negative controls, dead hepatocytes were similarly incubated in 7-ethoxyresorufin and these were used to set the background for the P450 EROD assay (see FIG. 10A).

Hepatocytes embedded in the polymer matrix both in an upstream portion (FIG. 10B) and a downstream portion of the reaction canal (FIG. 10C) were highly fluorescent, indicating that hepatocytes showed functionally active cytochrome P450 activities. The perfusion of the analyte into the polymer matrix via the original terpolymer port was effective and could be uptaken by the cells embedded in the matrix throughout the reaction canal.

EXAMPLE 3

This example illustrates the use of the polyelectrolyte complex coacervation reaction between methylated collagen as second charged polymer and terpolymer of HEMA-MMA-MM as first charged polymer to manipulate the formation of collagen matrices which have an important bearing on cellular behavior. Collagen of different methylation degrees is used to complex coacervate with terpolymer to alter polymer matrix morphology to engineer microenvironments for optimal cell support. Two liver-derived model cell types, primary hepatocytes and HepG2 cell line are chosen to study the effect of polymer matrix morphology on cellular functions. Primary hepatocytes represent primary cells that are highly sensitive, terminally differentiated and require specific chemical and topological extra-cellular matrix (ECM) cues for the maintenance of differentiated functions in vitro, while HepG2 is a hepatic cell line that represents transformed cell lines which can proliferate relatively easily in culture as long as no contact inhibition is encountered.

Collagen is modified to be cationic via methylation as described in Example 1. The degree of methylation is controlled by adjusting the reaction time and temperature. Briefly, the precipitated collagen is dissolved and stirred in acidified methanol for 4° C., 6 days (slightly methylated) and 23° C., 1 day (highly methylated) respectively and the degree of methylation is characterized by capillary zone electrophoresis. The capillary zone electrophoresis (CE) method has been developed for the quantification of the degree of collagen methylation.

Separations of different methylated collagens are performed on a CE-L1 System, from CE Resources Pte Ltd (Singapore). The polyvinyl alcohol (PVA) coated capillaries (50 μm ID×360 μm OD×70 cm length with 45 cm effective length) used are also obtained from CE Resources Pte Ltd (Singapore). Separations are run with 50 mM sodium phosphate buffer (pH 2.5) with 0.05% hydroxypropyl methyl cellulose (HPMC) at 21° C. Separation voltage is 22 kV and UV absorbance is detected at 200 nm. The collagen samples are introduced into the capillary by pressure (0.3 psi×15 s). PVA-coated capillaries are washed with distilled water for three minutes prior to the initial use. After initial conditioning, the coated capillaries are washed with distilled water for 1 min and 50 mM sodium phosphate buffer (pH 2.5) with 0.05% hydroxypropyl methyl cellulose (HPMC) for 3 min. between each analysis. All chemicals used are either of analytical grade or highest available purity. Hydrochloric acid, sodium phosphate, methanol and sodium hydroxide are obtained from Merck & Co. (NJ, USA). HPMC (VISC. 2 wt % in water, 5 CPS) was bought from Sigma-Aldrich Co. (St. Louis, Mo., USA). Acetone is purchased from Tedia Company Inc (Fairfield, OH, USA). All buffers and solutions are prepared with water purified through a Milli-Q system (Barnstead, Wiss., USA).

Figure 7:
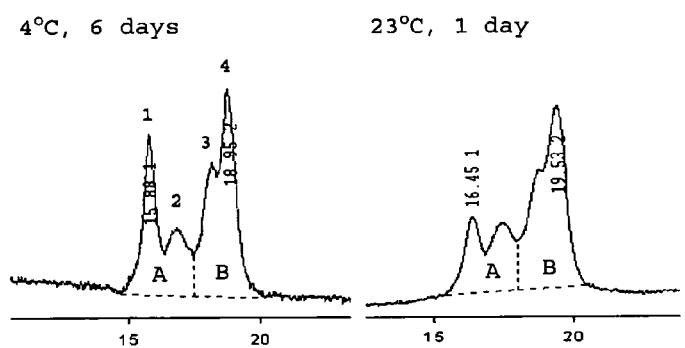
FIG. 7 illustrates the degree of collagen methylation characterized by the elution peaks of methylated collagen resolved by capillary electrophoresis. Based on this new method to quantify the degree of methylation, as described in Example 3, the CE index was developed on the basis of the data obtained from FIG. 7. The CE index characterizes the relative growth in the downstream peaks as increased degree of methylation. The CE index is calculated by dividing the area of the downstream peaks over that of the upstream peaks (Area B/Area A).

The methylated collagens are separated into four major bands (FIG. 7) that change with different methylation reaction conditions. An increase in collagen methylation correlates with a relative increase in the sizes of the downstream peaks. To quantify the degree of the collagen methylation, a CE index was developed which characterizes the relative growth in the downstream peaks as increased degree of methylation. The CE index is calculated by dividing the area of the downstream peaks over that of the upstream peaks (Area B/Area A in FIG. 7). An increase in collagen methylation correlates with an increase in the CE index (Table 4). The CE index of slightly methylated collagen is between 0.9 and 1.7 whereas the CE index of highly methylated collagen is between 1.7 and 2.5. Terpolymer of HEMA-MMA-MM was synthesized as described in Example 1.

TABLE 4

Capillary electrophoresis (CE) indices for two collagen methylation reactions. Degree of collagen methylation is characterized by the elution peaks of methylated collagen resolved by capillary zone electrophoresis.

| Collagen methylation | CE Index (area of B over A) |
| --- | --- |
| 4° C., 6 days | 1.40 |
| 23° C., 1 day | 1.90 |

For characterization studies of polymer matrix formation, 1.5 mg/ml methylated collagen is injected into and contacted with 3 wt % terpolymer using a syringe pump (30.5G needle), and confocal backscattering microscopy (Olympus Fluoview 500) is used to image the polymer matrix formed using a 60× water lens. Image-Pro Plus 4.5.1 was employed for the image processing and quantitative evaluation of matrix parameters.

For cell studies, hepatocytes are harvested from male Wistar rats by a two-step in situ collagenase perfusion as described previously (Seglen P. O., Methods Cell Biol. 1976, Vol. 13, P. 29-83) with some modifications. The cells are suspended in methylated collagen at a cell density of $5 \times 10^6$/ml (hepatocytes) or $8 \times 10^5$/ml (HepG2) before being injected into and contacted with terpolymer from a 30.G needle attached to a syringe pump. The hepatocytes and HepG2 cells supported by the polymer matrix are cultured in HepatoZYM-SFM (GIBCO Laboratories) and DMEM supplemented with fetal calf serum (10%) and HEPES (1 g/L) respectively in 37° C., 5% $CO_2$ humidified atmosphere. Hepatocytes detoxification functions are accessed by the 7-ethoxyresorufin-O-dealkylation (EROD) and 7-ethyoxycoumarin-O-deethylase (ECOD) activities of hepatocytes. Briefly, these involves the addition of 39.2 μM 7-ethoxyresorufin for 5h (EROD) and 0.26 mM 7-ethyoxycoumarin for 3h (ECOD), and the quantification of their metabolic products by confocal fluorescent microscopy (EROD) and High Performance Liquid Chromatography (HPLC) (ECOD). The proliferation of HepG2 cells over time is monitored by microscopy (Olympus Fluoview 500).

Figure 6:
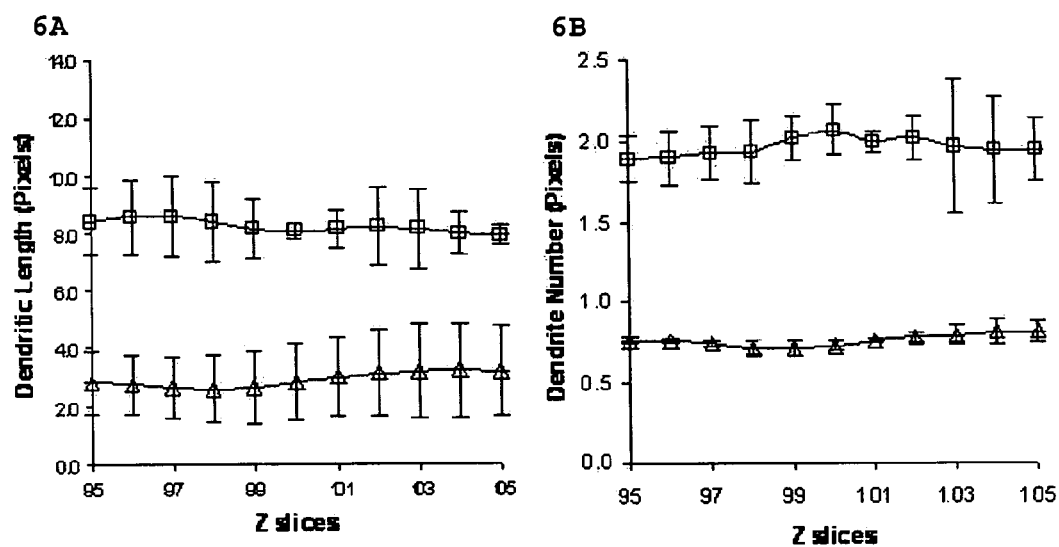
FIG. 6 shows the result of quantitative analyses of polymer matrix morphology (see Example 3): (A) Mean dendritic length per node; (B) Mean dendrite number per node [(□) Slightly methylated collagen; (Δ) Highly methylated collagen].

Thin, fragmented polymer matrices are formed by highly methylated collagen upon reaction with terpolymer (FIG. 5A), in contrast to the thick, connected polymer matrices formed by slightly methylated collagen (FIG. 5B). To quantify the effect of collagen methylation on matrix morphology, the mean dendritic length, defined as the average sum of the length of dendrites connected to each node per slice, and mean dendrite number, defined as the average sum of dendrites connected to each node per slice, are plotted for the ten centre slices in the z-stack (FIGS. 6A, 6B). From FIG. 6, the mean dendritic length and dendrite number for the highly methylated collagen (Δ), representative of fiber length and branching within the matrix respectively, are consistently below that of the slightly methylated collagen (□). Therefore, an increase in collagen methylation can be correlated with more fragmented matrix morphology.

Figure 9:
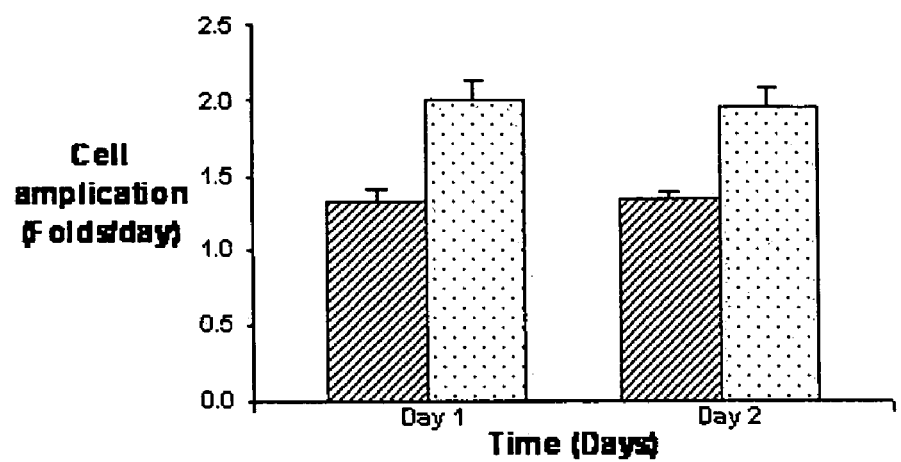
FIG. 9 illustrates the effect of collagen methylation (Example 3) on HepG2 proliferation. [(●) Slightly methylated collagen (CE index 1.4); (○) Highly methylated collagen (CE index 1.9)].

The detoxification functions of hepatocytes, indicated by their EROD and ECOD activities (FIGS. 8A, 8B), were significantly higher for all 4 days of culture when supported by the more connected polymer matrix formed by slightly methylated collagen (✼) compared to the polymer matrix formed by the highly methylated collagen (⋅). The ECOD scheme which employs HPLC for the measurement of metabolic products is a more precise assay that tests for the monooxygenase activities of more cytochrome P450 enzymes (CYP1A1, CYP2A6, CYP2C8-9, CYP2E1), but both EROD and ECOD assays detect significant differences in cytochrome enzyme activities in the two microenvironments. In contrast, HepG2 cell amplification in highly methylated collagen, defined as the ratio of cell number in microcapsule in $Day_{n+1}$ over $Day_n$, is greater than that of slightly methylated collagen by 1.5 times. On average, cell amplification for highly methylated (⋅) and slightly methylated (✼) collagen is 2 folds/day and 1.3 folds/day respectively (FIG. 9). Thus, the connected nano-fibers of the polymer matrix formed by slightly methylated collagen enhanced the differentiated functions of hepatocytes, while the fragmented nano-fibers formed by highly methylated collagen favored the proliferation of HepG2 cells.

Therefore, the proposed method of controlling polymer matrix formation by complex coacervation has been demonstrated to be capable of modulating matrix morphology to provide differential levels of cellular support. In particular, it has been shown that precise control of the polymer matrix structure supporting live cells is important in cellular support and functions because hepatocyte functions and HepG2 proliferation are selectively augmented in microenvironments with different polymer matrix connectivity.

EXAMPLE 4

The following example demonstrates how the variation of flow rates alters the formation of a three dimensional nano-fiber polymer matrix formed by laminar side-by-side flows of methylated collagen and terpolymer of hydroxylethyl methacrylate-methyl methacrylate-methyl acrylic acid (HEMA-MMA-MAA). Two flow configurations were used as can be seen from Table 5. In configuration 2, the time in which the laminar collagen stream was static (flow rate=0) was increased.

3 mg/ml methylated collagen and 3 wt % terpolymer modified and synthesized, as described in Example 1, were used as oppositely charged polymers. The PDMS canal was fabricated as described in Example 1. The two flow configurations used for the methylated collagen and terpolymer streams are given in Table 5.

TABLE 5

Volumetric flow rates of methylated collagen and terpolymer with respect to time for the two flow configurations.

| Methylated collagen flow rate in μl/h | Terpolymer flow rate in μl/h | Configuration 1 | Configuration 2 |
| --- | --- | --- | --- |
| | | Time in minutes | |
| 1000 | 1000 | 2 | 2 |
| 100 | 100 | 2 | 1 |
| 50 | 100 | 2 | 1 |
| 0 | 100 | 2 | 4 |

After the formation of the polymer matrix using the flow rates indicated in Table 5, the terpolymer stream was replaced with 1×PBS to be perfused at 200 μl/h in order to stop the polymerization reaction. Scanning electron microscopy (SEM) was used to characterize the collagen nano-fiber polymer matrix formed.

Figure 11:
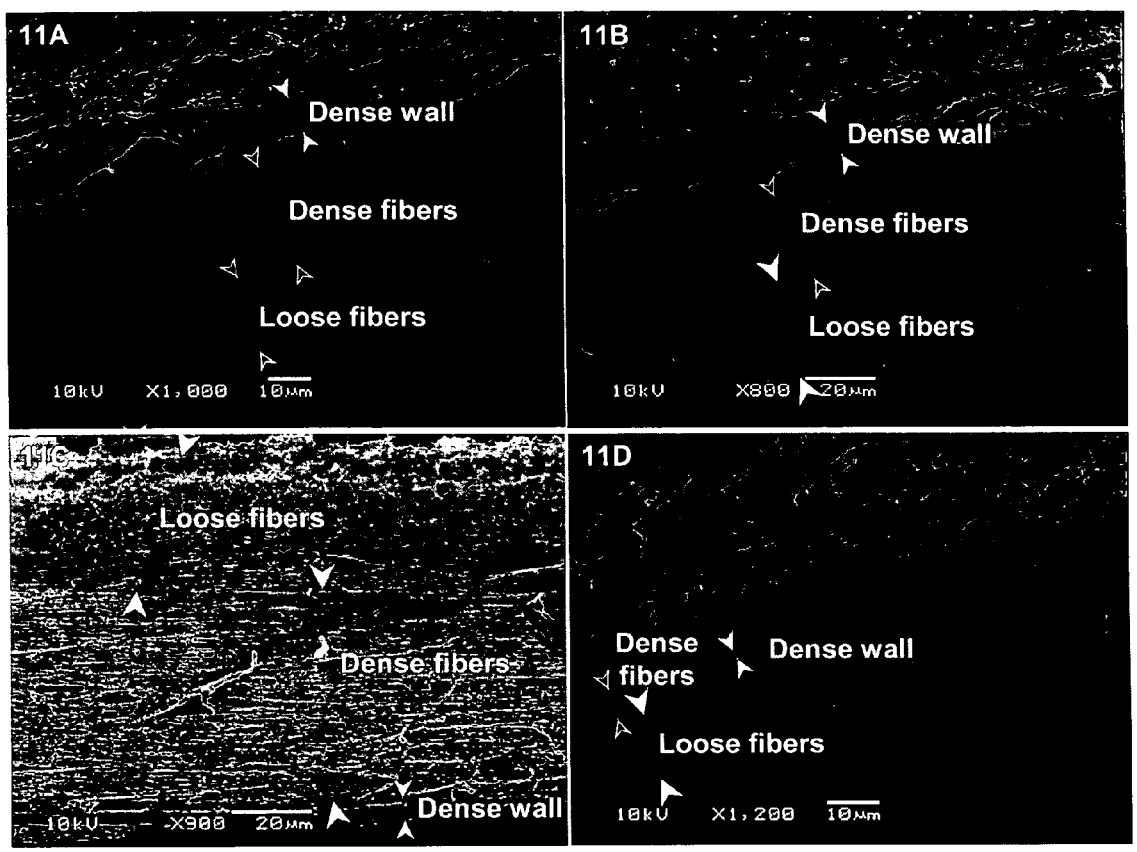
FIG. 11 illustrates the effect of altering the flow rates of the oppositely charged polymers in the reaction canal (Example 4). SEM micrographs of collagen nano-fiber matrix formed with the two flow configurations as described in Example 4. (A) and (B) configuration 1. (C) and (D) configuration 2. Flow configuration 2 resulted in more uniform loose fiber formation furthest away from terpolymer stream.

The collagen nano-fiber polymer matrix formed by both configurations can be loosely divided into 3 sections by the microstructures of the fibers formed in the polymer matrix: (i) dense wall, (ii) dense fibers, (iii) loose fibers (FIG. 11). The dense wall can be found at the interface at which the laminar collagen stream contacted with the laminar terpolymer stream, and the loose collagen fibers are formed furthest away from the laminar terpolymer stream facing the PDMS canal surface. It was found that flow configuration 2 which had greater static times for the collagen stream formed greater amounts of loose fibers and a cross-sectionally more uniform nano-fiber polymer matrix (FIGS. 11C and 11D), as compared to flow configuration 1 which had little loose fiber formation (FIGS. 11A and 11B).

What is claimed is:

1. A method for immobilizing at least one cell species in a matrix formed by biocompatible charged polymers comprising:
   Providing a first charged polymer and a second charged polymer, wherein the at least one cell species is embedded in the second charged polymer and wherein the first charged polymer has an electrical charge opposite to that of the second polymer;
   Reacting the polymers in a reaction canal of a flow device under laminar flow conditions to form a matrix for the at least one cell species.

2. The method of claim 1, wherein a prokaryotic or eukaryotic cell species is used as the at least one cell species.

3. The method of claim 2, wherein the eukaryotic cell species is selected from the group consisting of primary hepatocytes, HepG2, bone marrow mesenchymal cells, fibroblasts, chondrocytes, endothelial cells, epithelial cells, smooth muscle cells, lipocytes, neurons, osteoblasts, yeasts, amphibian cells, insect cells and plant cells.

4. The method of claim 2, wherein the prokaryotic cell species is selected form the group consisting of the genera *Eseherichia*, *Bacillus* and *Lactococcus*.

5. The method of claim 1, wherein the reaction canal of the flow device has one or more outlet openings and at least two inlet openings for the laminar polymer flows.

6. The method of claim 1, wherein charged polymers are used which form a matrix that can be perfused by liquids and is permeable to substances necessary to sustain the normal metabolic functions of the at least one cell species and to products released by the at least one cell species.

7. The method of claim 6, wherein the second charged polymer is selected from the group consisting of chitosan, methylated collagen, negatively charged collagen, carboxymethylcellulose (CMC) and polyanionic alginate.

8. The method of claim 7, wherein the first charged polymer is selected from the group consisting of positive or negatively charged terpolymer, $Ca^{2+}$, chondroitin sulfate A-chitosan and poly(L-lysine).

9. The method of claim 8, wherein methylated collagen and negatively charged terpolymer containing at least one of acrylic acid and methacrylic acid and at least one of hydroxyethyl methacrylate and hydroxylpropyl methacrylate are used as second charged polymer and first charged polymer, respectively.

10. The method of claim 9, wherein a terpolymer consisting of 25% 2-hydroxyethyl methacrylate, 25% methacrylic acid and 50% methyl metharylate (HEMA-MAA-MMA) is used as first charged polymer.

11. The method of claim 1, wherein the polymers are cross linked in the reaction of the polymers wherein the degree of cross linking can be altered by varying the charge of density of the polymers.

12. The method of claim 11, wherein a slightly methylated polymer and/or a highly methylated polymer is used, wherein the slightly methylated polymer has a charge density of between 0.9 and 1.7 CE and the highly methylated polymer has a charge density of between 1.7 and 2.5 CE.

13. The method of claim 1, wherein the polymers are cross linked in the reaction of the polymers wherein the degree of cross linking can be altered by varying the polymer concentration.

14. The method of claim 1, wherein the polymers are cross linked in the reaction of the polymers wherein the degree of cross liking can be altered by varying the reaction time of the polymers.

15. The method of claim 14, wherein the reaction time of the polymers is between about 30 seconds to 8 minutes.

16. The method of claim 1, wherein said cells are immobilized in matrices formed by biocompatible charged polymers.

17. A method for immobilizing at least one cell species in a matrix formed by biocompatible charged polymers comprising: providing a first charged polymer and a second charged polymer, wherein the at least one cell species is embedded in the second charged polymer and wherein the first charged polymer has an electrical charge opposite to that of the second polymer;
   reacting the polymers in a reaction canal of a flow device under laminar flow conditions to form a matrix for the at least one cell species, wherein the matrix comprises matrix polymers arranged lying side-by-side in the same plane or stacked one above the other.

18. The method of claim 17 wherein the matrix comprises fibers.

19. The method of claim 18, wherein a prokaryotic or eukaryotic cell species is used as the at least one cell species.

20. The method of claim 18, wherein the eukaryotic cell species is selected from the group consisting of primary hepatocytes, HepG2, bone marrow mesenchymal cells, fibroblasts, chondrocytes, endothelial cells, epithelial cells, smooth muscle cells, lipocytes, neurons, osteoblasts, yeasts, amphibian cells, insect cells and plant cells.

21. The method of claim 18, wherein the prokaryotic cell species is selected form the group consisting of the genera *Eseherichia*, *Bacillus* and *Lactococcus*.

22. The method of claim 18, wherein the reaction canal of the flow device has one or more outlet openings and at least two inlet openings for the laminar polymer flows.

23. The method of claim 18, wherein charged polymers are used which form a matrix that can be perfused by liquids and is permeable to substances necessary to sustain the normal metabolic functions of the at least one cell species and to products released by the at least one cell species.

24. The method of claim 18, wherein the second charged polymer is selected from the group consisting of chitosan, methylated collagen, negatively charged collagen, carboxymethylcellulose (CMC) and polyanionic alginate.

25. The method of claim 18, wherein the first charged polymer is selected from the group consisting of positive or negatively charged terpolymer, $Ca^{2+}$, chondroitin sulfate A-chitosan and poly(L-lysine).

26. The method of claim 18, wherein methylated collagen and negatively charged terpolymer containing at least one of acrylic acid and methacrylic acid and at least one of hydroxyethyl methacrylate and hydroxylpropyl methacrylate are used as second charged polymer and first charged polymer, respectively.

27. The method of claim 18, wherein a terpolymer consisting of 25% 2-hydroxyethyl methacrylate, 25% methacrylic acid and 50% methyl metharylate (HEMA-MAA-MMA) is used as first charged polymer.

28. The method of claim 18, wherein the polymers are cross linked in the reaction of the polymers wherein the degree of cross linking can be altered by varying the charge of density of the polymers.

29. The method of claim 18, wherein a slightly methylated polymer and/or a highly methylated polymer is used, wherein the slightly methylated polymer has a charge density of between 0.9 and 1.7 CE and the highly methylated polymer has a charge density of between 1.7 and 2.5 CE.

30. The method of claim 18, wherein the polymers are cross linked in the reaction of the polymers wherein the degree of cross linking can be altered by varying the polymer concentration.

31. The method of claim 18, wherein the polymers are cross linked in the reaction of the polymers wherein the degree of cross liking can be altered by varying the reaction time of the polymers.

32. The method of claim 18, wherein the reaction time of the polymers is between about 30 seconds to 8 minutes.

33. The method of claim 18, wherein said cells are immobilized in matrices formed by biocompatible charged polymers.

* * * * *